(12) United States Patent
Hubbard et al.

(10) Patent No.: US 11,224,590 B2
(45) Date of Patent: Jan. 18, 2022

(54) COMPOSITIONS AND METHODS FOR TREATING SEVERE CONSTIPATION

(71) Applicant: ANJI PHARMACEUTICALS INC., Boxford, MA (US)

(72) Inventors: Brian K. Hubbard, Boxford, MA (US); Michael H. Serrano-Wu, Belmont, MA (US)

(73) Assignee: Anji Pharmaceuticals Inc., Boxford, MA (US)

( * ) Notice: Subject to any disclaimer, the term of this patent is extended or adjusted under 35 U.S.C. 154(b) by 72 days.

(21) Appl. No.: 16/355,085

(22) Filed: Mar. 15, 2019

(65) Prior Publication Data

US 2019/0282549 A1 Sep. 19, 2019

Related U.S. Application Data

(60) Provisional application No. 62/644,033, filed on Mar. 16, 2018.

(51) Int. Cl.
*A61P 1/10* (2006.01)
*A61K 31/444* (2006.01)
*A61K 31/4245* (2006.01)

(52) U.S. Cl.
CPC ........ *A61K 31/4245* (2013.01); *A61K 31/444* (2013.01); *A61P 1/10* (2018.01)

(58) Field of Classification Search
None
See application file for complete search history.

(56) References Cited

U.S. PATENT DOCUMENTS

| 8,835,451 B2 * | 9/2014 | Serrano-Wu | C07D 263/48 514/277 |
| 9,061,012 B2 * | 6/2015 | Meyers | A61P 17/00 |

FOREIGN PATENT DOCUMENTS

| WO | WO-2007126957 A2 | 11/2007 | |
| WO | WO-2008/148849 A2 | 12/2008 | |
| WO | WO-2009112445 A1 * | 9/2009 | ................ A61P 9/10 |
| WO | WO-2013/130370 A2 | 9/2013 | |
| WO | WO-2013169648 A1 * | 11/2013 | ......... A61K 31/4439 |
| WO | WO-2019/178492 A1 | 9/2019 | |

OTHER PUBLICATIONS

Meyers et al. "Effect of the DGAT1 Inhibitor Pradigastat on Triglyceride and ApoB48 Levels in Patients with Familial Chylomicronemia Syndrome". Lipids in Health and Disease. 2015, 14:8 (p. 1-9). (Year: 2015).*
Webster LR. "Opioid-Induced Constipation". Pain Medicine. 2015; 16:S16-S21. (Year: 2015).*
Gregorian et al. "Opioid-Induced Constipation: Clinical Guidance and Approved Therapies". US Pharm. 2017; 42(12):15-19. (Year: 2017).*
Haas et al. "DGAT1 Mutation is Linked to a Congenital Diarrheal Disorder". The Journal of Clinical Investigation. 2012; 122(12): 4680-4684. (Year: 2012).*
Takemoto et al. "Diacylglycerol Acyltransferase 1/2 Inhibition Induces Dysregulation of Fatty Acid Metabolism and Leads to Intestinal Barrier Failure and Diarrhea in Mice". Physiological Reports. 2020; 8:e14542. pp. 1-9. (Year: 2020).*
Wilson et al. "Lubiprostone in Constipation: Clinical Evidence and Place in Therapy". Ther Adv Chronic Dis. 2015; 6(2):40-50. (Year: 2015).*
Denison et al., "Proof of mechanism for the DGAT1 inhibitor AZD7687: results from a first-time-in-human single-dose study," Diabetes Obes Metab 15(2):136-143 (2012).
International Search Report and Written Opinion for International Application No. PCT/US2019/022499 dated Mar. 15, 2019.
Kulmatycki et al., "Evaluation of a potential transporter-mediated drug interaction between rosuvastatin and pradigastat, a novel DGAT-1 inhibitor," Int J Clin Pharmol Ther 53(5):345-355 (2015).
Brenner et al., "Efficacy and safety of linaclotide for opioid-induced constipation in patients with chronic noncancer pain syndromes from a phase 2 randomized study." Pain, 161(5): 1027-1036 (2020).
"A Proof of Concept Study of Pradigastat in Patients With Functional Constipation," Clinical Trials: NCT04620161 (10 pages) (2021).
Extended European Search Report for EP Application No. 19767984 dated Nov. 12, 2021.
Nakajima et al., "Discovery of an orally Bioavailable Benzimidazole Diacylglycerol Acyltransferase 1 (DGAT1) Inhibitor That Suppresses Body Weight Gain in Diet-Induced Obese Dogs and Postprandial Triglycerides in Humans," J Med Chem, 60(11): 4657-4664 (2017).

* cited by examiner

*Primary Examiner* — Leslie A. Royds Draper
(74) *Attorney, Agent, or Firm* — Foley Hoag LLP; David P. Halstead

(57) ABSTRACT

The present disclosure provides methods related to treating or preventing gastrointestinal dysfunction in a subject in need thereof, which include the use of a diacylglycerol O-acyltransferase 1 (DGAT1) inhibitor. The disclosure also provides pharmaceutical compositions comprising a DGAT1 inhibitor, or pharmaceutically acceptable salts or esters thereof, useful for the treatments described herein.

8 Claims, 3 Drawing Sheets

COMPOSITIONS AND METHODS FOR TREATING SEVERE CONSTIPATION

RELATED APPLICATION

This application claims a right of priority from and the benefit of an earlier filing date of U.S. Provisional Application No. 62/644,033, filed Mar. 16, 2018, which is hereby incorporated by reference herein in its entirety.

BACKGROUND

The use of opioids for treatment of chronic pain has increased dramatically over the past decade. Chronic pain is associated with cancer and noncancerous conditions. Approximately 20% of patients presenting to physician's offices in the United States with pain symptoms were prescribed opioids. China's prescriptions of opioids has grown approximately 21% each year from 2013 to present. Patients taking opioids for an extended period are at risk for developing opioid-induced constipation (OIC). It is estimated that 40-80% of patients taking opioids have OIC.

OIC is often unresponsive to typical treatments for constipation such as increased dietary fiber, fluid intake, or physical activity levels. The use of bulk-forming laxatives (e.g., psyllium, methylcellulose) and excessive dietary fiber intake may even be detrimental, as these agents can cause bowel obstruction and worsen fecal impaction. Stimulants may cause bowel irritation due to the propulsion of overly dry fecal material. Additionally, mineral oil has many safety issues, and decrease absorption of fat-soluble vitamins A, D, E, and K with prolonged use. The use of osmotics leads to electrolyte abnormalities and must be administered rectally for treatment of OIC. Prescription medications, such as Methylnaltrexone (Relistor®), which is administered by a subcutaneous injection, can cause severe stomach pain. Currently, Traditional Chinese Medicine (Xiao-Cheng-Qi Decoction) used in China to treat constipation has very limited benefit. There remains a need to identify a treatment for OIC that is both effective and has minimal side effects.

SUMMARY OF THE INVENTION

In certain aspects, the present disclosure provides methods for treating or preventing gastrointestinal dysfunction, especially constipation (e.g., OIC), in a subject in need thereof, comprising administering to the subject a therapeutically effective amount of a DGAT1 inhibitor, whereby symptoms of the gastrointestinal dysfunction are reduced.

DGAT1 (diacylglycerol acyltransferase 1) is an enzyme associated with triglyceride biosynthesis in the gut, liver and adipose tissue, and has been investigated as a potential target for the treatment of diabetes and cardiovascular disease. While the outcome of the trials using DGAT1 inhibitors was initially positive, the most common side effect was diarrhea. Later human genetics studies indicated diarrhea is associated with DGAT1 loss-of-function in humans.

In one aspect, use of a diacylglycerol O-acyltransferase 1 (DGAT1) inhibitor in manufacture of a medicament for treatment or prevention of gastrointestinal dysfunction is disclosed. In another aspect, a method of producing a pharmaceutical composition for treating or preventing opioid-induced constipation is disclosed, e.g., by mixing a DGAT1 inhibitor with at least one substance, such as a carrier or excipient, to form the pharmaceutical composition. In another aspect, a pharmaceutical composition comprising a DGAT1 inhibitor for use in treatment or prevention of opioid-induced constipation is disclosed. In yet another aspect, a DGAT1 inhibitor for use in treatment or prevention of gastrointestinal dysfunction is disclosed. In one aspect, a method of treating or preventing gastrointestinal dysfunction in a non-human subject in need thereof is disclosed, which method includes administering to the subject a diacylglycerol O-acyltransferase 1 (DGAT1) inhibitor, after which symptoms of the gastrointestinal dysfunction are reduced. In an aspect, use of a DGAT1 inhibitor for treatment or prevention of gastrointestinal dysfunction is disclosed. In some aspects, a method of treating or preventing gastrointestinal dysfunction in a subject in need thereof is disclosed, which method includes administering to the subject a diacylglycerol O-acyltransferase 1 (DGAT1) inhibitor, and through which symptoms of the gastrointestinal dysfunction are reduced. In another aspect, a method of treating or preventing opioid-induced constipation in a subject in need thereof is disclosed, which includes administering to the subject a pharmaceutical composition comprising a DGAT1 inhibitor.

Each one of these aspects has various embodiments. For example, the gastrointestinal dysfunction can be constipation, such as chronic idiopathic constipation, irritable bowel syndrome with constipation, opioid-induced constipation, or constipation due to pregnancy, a medication, or a neurological disorder. In certain preferred embodiments, the constipation is opioid-induced constipation. Some embodiments of these aspects include conjoint administration with an opioid (e.g., medicament and opioid, DGAT1 inhibitor and opioid). The subject, in some embodiments, is receiving treatment with opioids. The DGAT1 inhibitor can be a small molecule, such as trans-4-(4-(5-((6-(trifluoromethyl)pyridin-3-yl)amino)pyridin-2-yl)phenyl)cyclohexane acetic acid (pradigastat) or a pharmaceutically acceptable salt or ester thereof, or 3-(4-(6-(5-(4-methoxyphenyl)-1,3,4-oxadiazol-2-yl)-1H-benzo[d]imidazol-2-yl)-3,5-dimethylphenyl)-2,2-dimethylpropanoic acid (compound 9) or a pharmaceutically acceptable salt or ester thereof. In other embodiments, the DGAT1 inhibitor is an antibody. In various embodiments, the compositions and methods disclosed herein are for treatment of a human (e.g., the subject is a human).

DETAILED DESCRIPTION OF THE INVENTION

Figure 1:
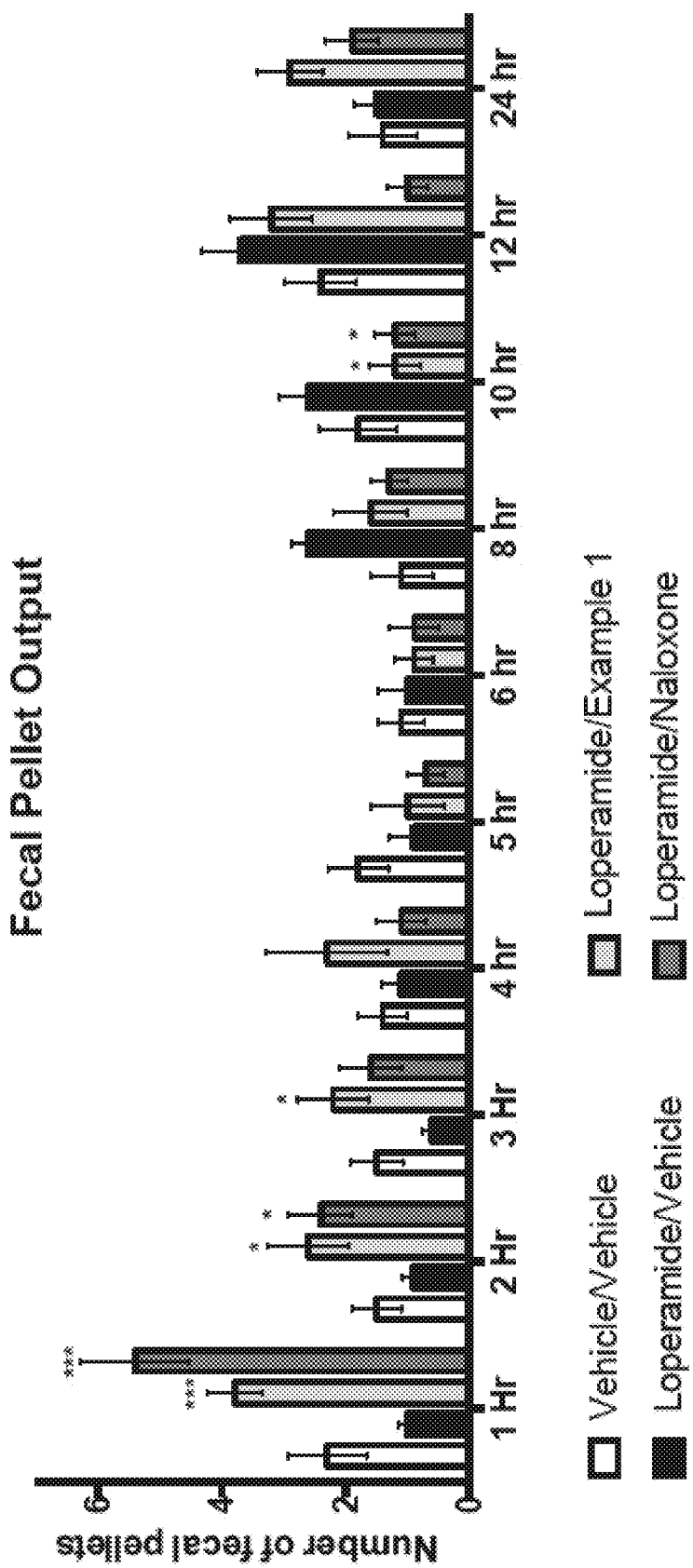
FIG. 1 shows fecal pellet count output (FPCO) in the model of loperamide-induced constipation. Animals were dosed with 10 mg/kg of loperamide throughout the study. Product 1 was administered during day 4 through day 7 of the study. On the final study day (day 7), mice were dosed with Vehicle, Product 1 (30 mg/kg), or Naloxone (1 mg/kg), and FPCO was measured for 24 hours. This figure uses the label "Example 1" to refer to Product 1, and shows the bars for each time point in the following order from left to right: Vehicle/Vehicle→Loperamide/Vehicle→Loperamide/Product 1→Loperamide/Naloxone. ***P<0.001; *P<0.05 compared to Loperamide/Vehicle group; n=10/group. Two-way ANOVA with post-hoc Fisher's LSD test.

In certain aspects, the present disclosure provides methods for treating or preventing gastrointestinal dysfunction in a subject in need thereof, comprising administering to the subject a therapeutically effective amount of a DGAT1 inhibitor, wherein symptoms of gastrointestinal dysfunction are reduced. In preferred embodiments, the gastrointestinal dysfunction is constipation. The constipation may be chronic idiopathic constipation, irritable bowel syndrome with constipation, opioid-induced constipation (OIC), or constipation due to pregnancy, medications, or a neurological disorder (e.g., autonomic neuropathy, diabetic-related neuropathy, multiple sclerosis, spinal cord injury, or stroke). In particularly preferred embodiments, the constipation is opioid-induced constipation. In certain embodiments, the subject is a subject who receives treatment with opioids chronically.

In some embodiments, the DGAT1 inhibitor is a small molecule. In some embodiments, the DGAT1 inhibitor is 2-(4-(4-(5-((6-(trifluoromethyl)pyridin-3-yl)amino)pyridin-2-yl)phenyl)cyclohexyl)acetic acid (e.g., trans-4-(4-(5-((6-(trifluoromethyl)pyridin-3-yl)amino)pyridin-2-yl)phenyl) cyclohexane acetic acid (pradigastat), or any mixtures (e.g., mixtures of cis and trans isomers) thereof). In yet other embodiments, the DGAT 1 inhibitor is 3-(4-(6-(5-(4-methoxyphenyl)-1,3,4-oxadiazol-2-yl)-1H-benzo[d]imidazol-2-yl)-3,5-dimethylphenyl)-2,2-dimethylpropanoic acid (compound 9). In still other embodiments, the DGAT1 inhibitor is an antibody, a portion of an antibody, a mimetic of an antibody, or variants/combinations thereof (e.g., mAb, F(ab')$_2$, Fab, scFv, tandem di-scFv, tandem tri-scFv, diabody, tribody, sdAb (e.g., V$_{HH}$, V$_{NAR}$), affilin, affimer, affitin, alphabody, anticalin, avimer, DARPin, monobody, nanoC-LAMP).

In certain preferred embodiments, the subject is human.

In certain aspects, the present disclosure also provides pharmaceutical compositions comprising a DGAT1 inhibitor, or a pharmaceutically acceptable salt or ester thereof, useful for the methods described herein. In some embodiments, the composition is formulated for oral delivery. In other embodiments, the composition is formulated for rectal delivery. The composition may also be formulated for intravenous delivery.

In certain preferred embodiments, provided herein are methods for treating or preventing opioid-induced constipation in a subject in need thereof, comprising administering to the subject a therapeutically effective amount of a pharmaceutical composition disclosed herein.

DGAT and DGAT1 Inhibitors

Diacylglycerol acyltransferase (DGAT) is a microsomal enzyme that plays a central role in the metabolism of cellular glycerolipids. DGAT catalyzes the final step in triacylglycerol (TAG) biosynthesis by converting diacylglycerol and fatty acyl-coenzyme A into triacylglycerol. DGAT plays a fundamental role in the metabolism of cellular diacylglycerol and is important in higher eukaryotes for physiologic processes involving triacylglycerol metabolism such as intestinal absorption, lipoprotein assembly, adipose tissue formation, and lactation.

There are two isozymes of DGAT encoded by the genes DGAT1 and DGAT2. Although both isozymes catalyze similar reactions, they have no sequence homology to each other. DGAT1 is mainly located in absorptive enterocyte cells that line the intestine and duodenum where it reassembles triglycerides that were decomposed through lipolysis in the process of intestinal absorption. DGAT1 reconstitutes triglycerides in a committed step after which they are packaged together with cholesterol and proteins to form chylomicrons. DGAT2 is mainly located in fat, liver and skin cells.

Pradigastat (LCQ-908) is a representative inhibitor of DGAT1, and a structure of which is shown below:

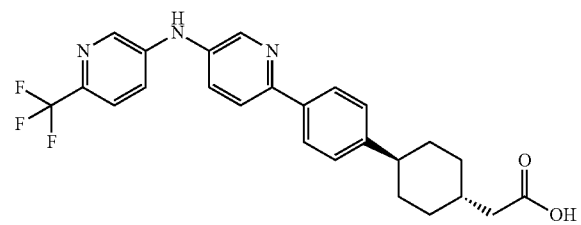 [SMILES: O=C(O)C[C@H]1CC[C@H](c2ccc(-c3ccc(Nc4ccc(C(F)(F)F)nc4)cn3)cc2)CC1]

Another selective DGAT1 inhibitor, PF-04620110, is disclosed in "Discovery of PF-04620110, a Potent, Selective, and Orally Bioavailable Inhibitor of DGAT-1," ACS Med. Chem. Lett. 2011, 2, 407-412, and a structure of which is shown below:

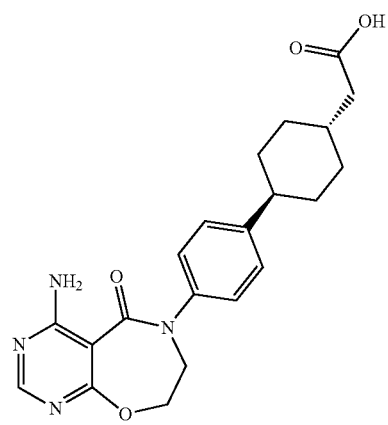 [SMILES: Nc1ncnc2c1C(=O)N(c1ccc([C@H]3CC[C@H](CC(=O)O)CC3)cc1)CCO2]

Another DGAT1 inhibitor is JTT-553, a structure of which appears below:

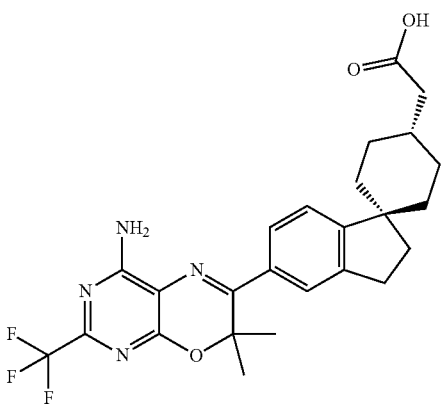 [SMILES: CC1(C)Oc2nc(C(F)(F)F)nc(N)c2N=C1c1ccc2c(c1)CC[C@]21CC[C@@H](CC(=O)O)CC1]

Another DGAT1 inhibitor is AZD-7687, a structure of which appears below:

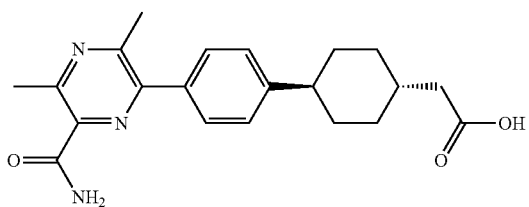 [SMILES: Cc1nc(C)c(-c2ccc([C@H]3CC[C@H](CC(=O)O)CC3)cc2)nc1C(N)=O]

Another DGAT1 inhibitor is Compound 9, a structure of which appears below:

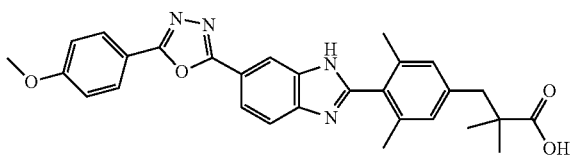 [SMILES: COc1ccc(-c2nnc(-c3ccc4nc(-c5c(C)cc(CC(C)(C)C(=O)O)cc5C)[nH]c4c3)o2)cc1]

Other suitable DGAT1 inhibitors include the DGAT1 inhibitors described in: WO04047755, WO0204682, WO9745439, US20030154504, US20030167483, WO9967403, WO9967268, WO05013907, WO05044250, WO06064189, WO06004200, WO06019020, US20040209838, US20040185559, WO04047755, US20040224997, WO05072740, JP2006045209, WO06044775, JP2004067635, JP2005206492, U.S. Pat. No. 6,100,077, WO04100881, WO06113919, WO072740, WO09126624, WO022551, and WO07141545, their salts or esters, etc. These patents and publications are incorporated by reference herein in their entireties, and in particular for their disclosure of DGAT1 inhibitors.

The methods and compositions of the present disclosure relate to the use of a DGAT1 inhibitor, or a pharmaceutically acceptable salt or ester thereof. The DGAT1 inhibitor useful in the compositions disclosed herein may be any suitable DGAT1 inhibitor. The DGAT1 inhibitor may be peptidal or non-peptidal in nature; however, the use of a non-peptidal DGAT1 inhibitor is preferred, e.g., for convenience of administration.

Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The terms "administration" and or "administering" should be understood to mean providing a compound or a prodrug of a compound to a subject in need of treatment.

The phrase "pharmaceutically-acceptable carrier" as used herein means a pharmaceutically acceptable material, composition or vehicle, such as a liquid or solid filler, diluent, excipient, solvent, or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "subject" refers to a mammal, including, but not limited to, a human or non-human mammal, such as a bovine, equine, canine, ovine, or feline.

The term "substance" includes all ingredients that can be included in a pharmaceutical composition (e.g., water, other solvents, carriers, excipients).

The terms "conjoint" and "conjointly," in the context of administering compounds or compositions, indicate that two different compounds or compositions can be administered without separating their administration regimens from each other or without ceasing administration of one before starting the administration of the other one (e.g., they can be administered via an agent that includes both, they can otherwise be administered concurrently, they can be administered separately but without a significant time delay (e.g., 1 hour, 6 hours, 12 hours, 1 day, 2 days) between their administrations).

As used herein, the term "treating" or "treatment" includes reversing, reducing, or arresting the symptoms, clinical signs, and underlying pathology of a condition in a manner to improve or stabilize a subject's condition.

The term "therapeutic treatment" is art-recognized and includes administering to the subject a composition after the manifestation of an unwanted condition, such as OIC.

Therapeutic Methods

Provided herein are methods of treating or preventing gastrointestinal dysfunction in a subject by administering to the subject a therapeutically effective amount of a DGAT1 inhibitor. In some embodiments, the methods relate to treating constipation in the subject. In certain embodiments, the constipation is opioid-induced constipation. Also provided are methods of treating opioid-induced constipation in a subject in need thereof, comprising administering to the subject a therapeutically effective amount of a pharmaceutical composition disclosed herein.

Compositions

In some aspects, the invention relates to a pharmaceutical composition comprising a DGAT1 inhibitor. The composition may comprise a pharmaceutically acceptable carrier. The pharmaceutical composition disclosed herein may be delivered by any suitable route of administration, including orally, buccally, sublingually, parenterally, and rectally, as by powders, ointments, drops, liquids, gels, tablets, capsules, pills, or creams. In certain embodiments, the pharmaceutical compositions are delivered generally (e.g., via oral administration). In certain other embodiments, the compositions disclosed herein are delivered rectally. In some embodiments, the compositions disclosed herein are delivered intravenously.

Actual dosage levels of the active ingredients in the pharmaceutical compositions may be varied to obtain an amount of the active ingredient that is effective to achieve the desired therapeutic response for a subject, composition, and mode of administration, without being toxic to the subject.

For example, pradigastat may be administered at a dose of about 5 mg to about 40 mg, e.g., at a dose of about 5 mg, about 10 mg, about 15 mg, about 20 mg, or about 40 mg. Similarly, compound 9 may be administered at a dose of about 50 mg to about 600 mg, e.g., at a dose of about 50 mg, about 150 mg, about 300 mg, about 450 mg, or about 600 mg.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

EXAMPLE

Materials

Product 1 (CAS No: 956136-95-1), loperamide, and naloxone were each purchased from commercial vendors and used directly without further purification.

Mouse Model of Loperamide-Induced Constipation

Male C57BL mice (6 to 8 weeks, 25-30 grams) were placed on high-fat diet (45% fat) and allowed to acclimate (singly housed on a 12 hr light/dark cycle) for 6 days. Loperamide was administered by oral gavage at 10 mg/kg (10% DMSO/90% of 20% SBE-ß-CD in saline) for 3 consecutive days prior to study initiation.

Methods

Daily loperamide dosing was continued throughout the entire study. On the $4^{th}$ day of loperamide administration, Product 1 (30 mg/kg in 10% DMSO/90% of 20% SBE-ß-CD in saline) was administered 30 minutes later by oral gavage. Sequential treatment of loperamide and Product 1 (30 minutes post-loperamide dose) was continued for 2 additional days. On the final day of the study, a fourth group of animals received a single subcutaneous administration of naloxone (1 mg/kg) as a positive control.

On the final study day, the number of fecal pellets and pellet weights for each animal were recorded hourly for the 6 hours following dosing. Fecal pellet output was then recorded every other hour for the period of 6-12 hours post-dosing. Additionally, total fecal pellet count for the period of 12 to 24 hours was measured. Fecal pellets were dried for 24 hours and dry weight recorded.

Prism software (GraphPad Prism, San Diego, Calif.) was employed for graphs and curve fitting. Data was analyzed using a two-way ANOVA with post-hoc LSD test.

Results

Figure 2:
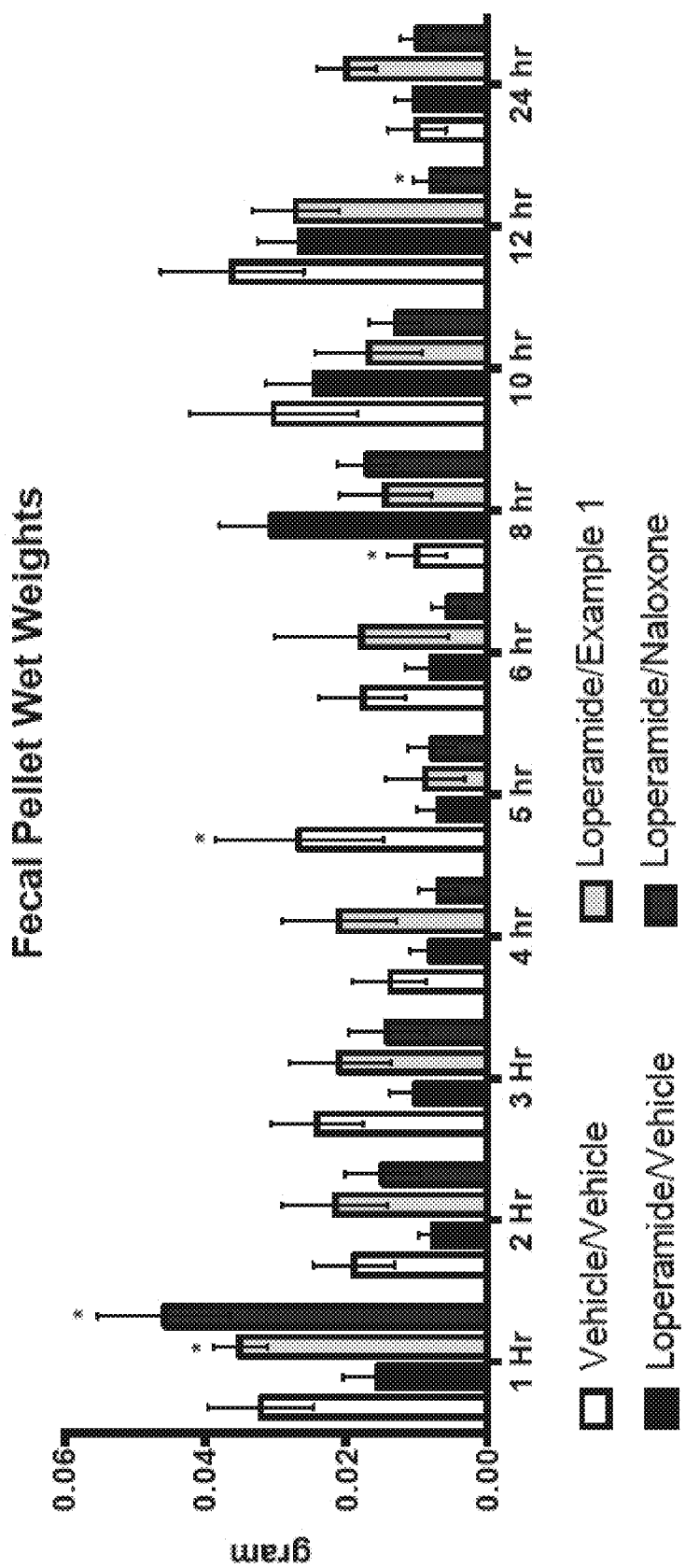
FIG. 2 shows fecal pellet wet weights (FPWW) in the model of loperamide-induced constipation. Animals were dosed with 10 mg/kg of loperamide throughout the study. Product 1 was administered during day 4 through day 7 of the study. On the final study day (day 7), mice were dosed with Vehicle, Product 1 (30 mg/kg), or Naloxone (1 mg/kg), and FPWW was measured for 24 hours. This figure uses the label "Example 1" to refer to Product 1, and shows the bars for each time point in the following order from left to right: Vehicle/Vehicle→Loperamide/Vehicle→Loperamide/Product 1→Loperamide/Naloxone. *P<0.05 compared to Loperamide/Vehicle group; n=10/group. Two-way ANOVA with post-hoc Fisher's LSD test.
Figure 3:
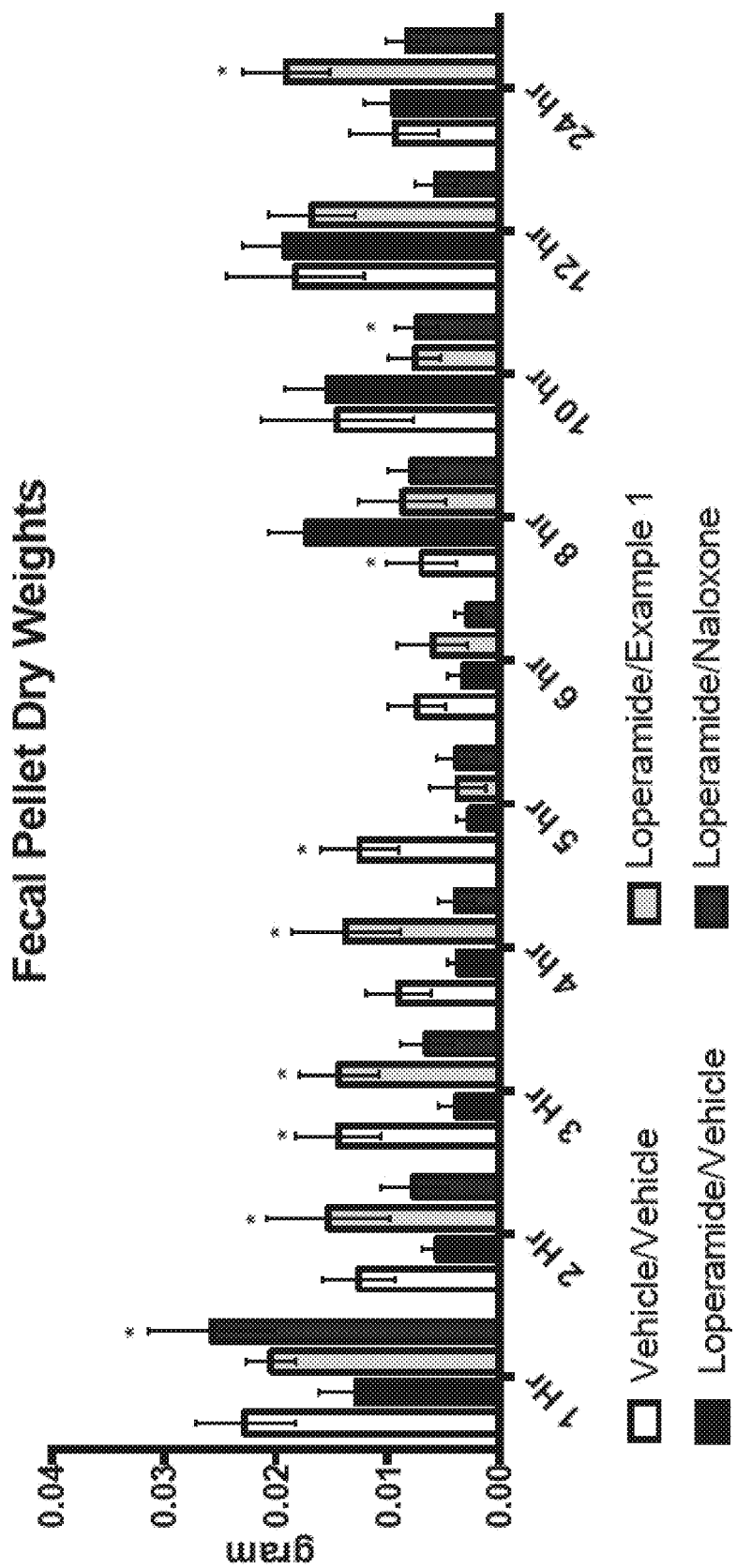
FIG. 3 shows fecal pellet dry weights (FPDW) in the model of loperamide-induced constipation. Animals were dosed with 10 mg/kg of loperamide throughout the study. Product 1 was administered during day 4 through day 7 of the study. On the final study day (day 7), mice were dosed with Vehicle, Product 1 (30 mg/kg), or Naloxone (1 mg/kg), and FPDW was measured for 24 hours. This figure uses the label "Example 1" to refer to Product 1, and shows the bars for each time point in the following order from left to right: Vehicle/Vehicle→Loperamide/Vehicle→Loperamide/Product 1→Loperamide/Naloxone. *P<0.05 compared to Loperamide/Vehicle group; n=10/group. Two-way ANOVA with post-hoc Fisher's LSD test.

The results from the study demonstrate that administration of Product 1 at 30 mg/kg produced a significant increase in fecal pellet output, wet and dry weights of fecal pellets in the first 1-4 hours (FPCO, FIG. 1) or 1-4 hours (wet and dry weights, FIG. 2 and FIG. 3) after compound administration. The figures use the label "Example 1" to refer to Product 1.

INCORPORATION BY REFERENCE

Each publication and patent mentioned herein is hereby incorporated by reference in its entirety. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of opioid-induced constipation in a subject in need thereof, the method comprising administering to the subject a pharmaceutical composition comprising trans 4-(4-(5-((6-(trifluoromethyl)pyridin-3-yl)amino)pyridin-2-yl)phenyl)cyclohexane acetic acid (pradigastat) or a pharmaceutically acceptable salt or ester thereof.

2. The method of claim 1, wherein the subject is receiving treatment with opioids.

3. The method of claim 1, further comprising conjointly administering an opioid to the subject.

4. The method of claim 1, wherein the subject is a human.

5. A method of treating opioid-induced constipation in a subject in need thereof, the method comprising administering to the subject a pharmaceutical composition comprising trans-4-(4-(5-((6-(trifluoromethyl)pyridin-3-yl)amino)pyridin-2-yl)phenyl)cyclohexane acetic acid (pradigastat) or a pharmaceutically acceptable salt thereof.

6. The method of claim 5, wherein the subject is receiving treatment with opioids.

7. The method of claim 5, further comprising conjointly administering an opioid to the subject.

8. The method of claim 5, wherein the subject is a human.

* * * * *

UNITED STATES PATENT AND TRADEMARK OFFICE
CERTIFICATE OF CORRECTION

| | |
|---|---|
| PATENT NO. | : 11,224,590 B2 |
| APPLICATION NO. | : 16/355085 |
| DATED | : January 18, 2022 |
| INVENTOR(S) | : Brian K. Hubbard et al. |

It is certified that error appears in the above-identified patent and that said Letters Patent is hereby corrected as shown below:

In the Claims

In Claim 1, at Column 8, Line 43, "A method of opioid-induced constipation in a subject" should read --A method of treating opioid-induced constipation in a subject--

Signed and Sealed this
Thirty-first Day of January, 2023

Katherine Kelly Vidal
*Director of the United States Patent and Trademark Office*